United States Patent [19]

Hosoi et al.

[11] Patent Number: 4,851,146
[45] Date of Patent: Jul. 25, 1989

[54] PHOSPHONIC ACID DERIVATIVE BASED AGENTS FOR CLEANING AND DISSOLVING TARTAR OF REMOVABLE ORAL PROSTHESES

[75] Inventors: Toshio Hosoi, Tokyo; Kazuhiro Watanabe, Kamifukuoka, both of Japan

[73] Assignee: G-C Dental Industrial Corp., Tokyo, Japan

[21] Appl. No.: 51,758

[22] Filed: May 20, 1987

[30] Foreign Application Priority Data

Jun. 11, 1986 [JP] Japan ................. 61-133703

[51] Int. Cl.$^4$ .......... A61K 7/30; C11D 3/36; C11D 7/36
[52] U.S. Cl. .................. 252/102; 252/80; 252/82; 252/142; 252/174.16; 252/545; 252/DIG. 11; 252/DIG. 18; 424/54; 424/57; 514/836
[58] Field of Search .......... 252/DIG. 11, 80, 82, 252/174.16, 545, 148, 151, 95, 100, 102, 142, DIG. 17; 424/57, 54; 514/836

[56] References Cited

U.S. PATENT DOCUMENTS

| | | | |
|---|---|---|---|
| 3,934,002 | 1/1976 | Haefele | 424/54 |
| 3,959,458 | 5/1976 | Agricola et al. | 424/52 |
| 4,540,504 | 9/1985 | Edga | 252/102 |
| 4,701,223 | 10/1987 | Eoga | 134/2 |

FOREIGN PATENT DOCUMENTS

| | | |
|---|---|---|
| 1110987 | 4/1968 | United Kingdom . |
| 2090855 | 7/1982 | United Kingdom . |
| 2095694 | 10/1982 | United Kingdom . |

OTHER PUBLICATIONS

Monsanto Technical Bulletin No. IC:SCS-320 "Dequest ® 2000 and 2006 Phosphonates for Scale and Corrosion Control, Chelation, Dispersion".
Monsanto Technical Bulletin No. IC/SCS-314 "Cooling Water Corrosion Inhibition with Dequest ® Organo Phosphorus Compounds".
Monsanto Technical Bulletin No. IC/SCS-313 "Dequest ® 2010 Organophosphorus Product for Scale Prevention & Corrosion Inhibition in Water Treatment".
Chemical Abstracts No. 99:64269w [Gaffar et al.] Aug. 1983.
Chemical Abstracts No. 99:152042x [Naguchi et al.] Nov. 1983.
Chemical Abstracts No. 100:151005q [Wolltgens] May 1984.
Chemical Abstracts No. 106:12943e [Fukuda et al.] Jan. 1987.

Primary Examiner—Paul Lieberman
Assistant Examiner—Linda D. Skaling
Attorney, Agent, or Firm—Oblon, Spivak, McClelland, Maier & Neustadt

[57] ABSTRACT

An agent for cleaning and dissolving tartar or removable oral prostheses comprises a solution of a phosphonic acid base chelating agent or agents as the active agents in water, the phosphonic acid base chelating agent or agents being selected from the group consisting of aminotrimethylphosphonic acid, hydroxyethylidenephosphonic acid and ehtylenediaminetetramethylphosphonic acid as well as their alkali metal salts, and being contained in water in an amount of 15 to 90 weight %, the solution being of a pH of 7 or lower.

3 Claims, No Drawings

PHOSPHONIC ACID DERIVATIVE BASED AGENTS FOR CLEANING AND DISSOLVING TARTAR OF REMOVABLE ORAL PROSTHESES

BACKGROUND OF THE INVENTION

1. Field of the Invention

The present invention relates to an agent for cleaning and dissolving dental calculuses or tartar (hereinafter simply called the tartar) of removable oral prostheses, which comprises a phosphonie acid base chelating agent or agents contained in water.

Removable oral prostheses serve in the mouth to recover occlusal, pronouncing and masticating functions, and are attachable thereinto or detachable therefrom by simple manipulation. Full or partial dentures are typically mentioned for that purpose. Materials consist of such prostheses may include porcelain, methacrylic resins, sulfone resins, gold alloys, silver alloys, gold-silver-palladium alloys, nickel-chromium alloys and cobalt-chromium alloys etc. While such oral prostheses are present in the mouth, dental plaque is deposited thereon under the influence of sputum, food residues, bacteria and so on, and is then calcified, leading to deposition of tartar on the oral prostheses.

Such deposits contaminate the prostheses per se. In addition, they not only worsen the oral environment, but are unpreferred for the health of a manipulator who corrects or restores the prostheses.

In order to maintain the oral health of a prosthesis-carrying individual, it is essentially required to remove plaque or tartar deposited thereon, and it is one of important manipulations for a dentist or a detal technician to remove plaque or tartar at the time of the correction or restoration of prostheses or regular examination. The present invention provides a composition for easily removing plaque or tartar on oral prostheses within a short time and without inflicting any damage thereon.

2. Statement of the Prior Art

Heretofore, cleaning agents designed to remove tartar deposited on the removable oral prostheses have relied upon (1) a polishing action, (2) a chemical action and (3) a combination of the polishing action with the chemical action.

According to the polishing type technique, tartar is removed by using a brush with finely divided silica, alumina, calcium phosphate and the like. This technique requires a longer period of time for removal of tartar, and may possibly wear out the prostheses. On the other hand, the conventional chemical type technique makes use of an aqueous solution containing peroxides, chloric acid compounds, EDTA, disinfectants, enzymes and so on. However, this technique is effective for removal of new tartar, but is uneffective for removal of old one. For that reason, the old tartar should be removed by immersing the corresponding prosthesis in an aqueous solution of an acid such as hydrochloric, acetic or phosphoric acid. However, this has the disadvantage of corroding and discoloring the metal forming the prosthesis.

SUMMARY OF THE INVENTION

As mentioned above, it is essentially required for a dentist or a dental technician to remove plaque and tartar deposited on the prosthesis placed in the mouth for an extended peirod of time, when repairing or regulating it. Therefore, a main object of the present invention is to provide a novel composition for removing plaque or tartar deposited on prostheses within a short time and without inflicting any damage thereon such as wearing-off or discoloration and so on.

Tartar is deposited on prostheses placed in the mouth for an extended period of time without application of any pertinent maintenance. Such tartar is considered to result from calcification of deposits in the mouth, and is found to be composed mainly of calcium phosphate and further contain calcium carbonate, magnesium phosphate, protein, fats and the like.

According to the present invention, a composition containing a phosphate base chelating agent or agents as the main component is allowed to act upon a metal salt insoluble in water such as calcium phosphate, calcium carbonate and magnesium phosphate to solubilize and thereby dissolve it in water for its removal.

A particular advantage of the present invention is to achieve removal of tartar within a short period of time, which has been impossible in the prior art, but without inflictng any damage on the material forming oral prostheses.

The composition according to the present invention is characterized by containing a phosphonic base chelating agent or agents as the main component, and the object of the present invention is achieved by making use of a rapid chelating reaction of said chelating agent(s), through which an insoluble metal salt is solubilized.

Water is inevitable for the tartar-dissolving agent according to the present invention so as to attain its object by making use of the chelating ability of the phosphonic base chelating agent(s), thereby to solubilize the tartar components in water. Thus, the present agent is provided in the form of an aqueous solution.

The compositions according to the present invention are characterized by containing the phosphonic base chelating agent or agents in water. The phosphonic base chelating agents used in the present invention and known in the art may include aminotrimethylphosphonic acid or its alkali metal salt, hydroxyethylidenediphosphonic acid or its alkali metal salt, and ethylenediaminetetramethylphosphonic acid or its alkali metal salt.

DETAILED DESCRIPTION OF THE INVENTION

The present invention will now be explained in further detail.

Preferably, the compositions of the present invention should contain the phosphonic base chelating agent or agents at a concentration of 10 to 90 weight %, more particularly 15 to 70 weight %. At a lower concentration of below 10 weight %, the rate of dissolution is too slow to dissolve tartar within a short period of time. At a higher concentration exceeding 90 weight %, on the other hand, it is likely that the starting materials forming dentures, such as a silver alloy, may be discolored.

The agents for cleaning and dissolving tartar of removable oral prostheses, according to the present invention, may further contain polyphosphates having a chelating ability, known chelating agents, detergents and surfactants expected to show a cleaning action, peroxides, chloric acid compounds and enzymes as well as other disinfectants, deodorants, deodorizers and perfumes.

Depending upon their types, the phosphonic base chelating agents are found to show a unique solubility with respect to calcium carbonate and phosphate that are the components of tartar. For instance, the results of measurement of the amount of dissolution within a certain time have indicated that hydroxyethylidenediphosphonic acid shows the maximum amount of dissolution in calcium phosphate. It has been found, on the other hand, that ethylenediaminetetramethylphosphonic acid shows the maximum amount of dissolution in calcium carbonate. From the result of dissolution of the tartar taken out of the mouth, it has also been observed that the type of the phosphonic base chelating agents to be used depends upon a difference in the process of development thereof. For that reason, use of two or more phosphonic base chelating agents should be preferred for the purpose of offsetting such a difference in the tartar. In limited applications, however, sufficient effects would be obtained with one phosphonic base chelating agent.

The tartar-dissolving agent according to the present invention may be adjusted in terms of pH by combination with the phosphonic base chelating agent or agents or use of additives. In an alkaline state where pH exceeds 7, however, the dissolution of tatar is too slow to remove it within a short period of time. It is therefore preferred to select the compositions in such a way that they show a pH value of 7 or lower.

In use, a dentist takes a removable oral prosthesis from within the mouth of a patient, and immerses it in the invented tartardissolving agent filled in a beaker to remove the tartar deposited thereon. Use of an ultrasonic cleaner causes rapid dissolution of the tartar, thus resulting in removal thereof.

The agents for cleaning and dissolving tartar of removable oral prostheses, according to the present invention, make it possible to dissolve and remove tartar within a short period of time, and is thus timesaving for both dentists and patients. Furthermore, the agents of the present invention prevent a manipulator from suffering from bacterial infection, etc., and are thus advantageous in view of health, since the removal of tartar can be achieved, while the prosthesis is kept intact.

EXAMPLES

Example 1

Aminotniethylphosphonic acid: 23.5 weight %
Hydroxyehylidenediphosphonic acid: 15.6 weight %
Purified water: 58.7 weight %
Polyoxyethylenenonyl phenyl ether: 0.2 weight %
Deodorant (Trade Name - FS-500M —, manufactured by Nippon Phirine Co., Ltd.): 2.0 weight %

The aforesaid materials were mixed together under agitation to prepare a solution. Apart from this, a full denture comprising porcelain and methacrylic resin and found to have tartar deposits thereon was removed from within the mouth of a patient, and was washed with water, following which the water was wiped out by gauze. By measurement, it was found to weigh 16.25 g. The denture was immersed in 100 g of said solution, and was subjected to vibration with an ultrasonic cleaner (available under the trade name of Ultrasonic Cleaner MU-III manufactured by GC Dental Industrial Corp.) for 20 minutes. Visual observation of the full denture withdrawn from the solution indicated that the tartar deposits were completely removed, and that the materials forming the full denture did not show any sign of abnormality. After the full denture had been washed with water, followed by removal of the water by gauze-wiping, it was found to weigh 15.93 g, which indicated that a weight loss corresponding to the tartar deposits was 0.32 g.

Example 2

A solution was prepared by mixing under agitation 65 weight % of hydroxyethylidenediphosphonic acid with 35 weight % of purified water. Apart from this, a partial denture comprising a gold-silver-palladium alloy and methacrylic resin, on which new tartar was found to be deposited, was removed from within the mouth of a patient, and was washed with water, after which the water was wiped out by gauze. By measurement, that denture was found to weigh 10.04 g. The denture was immersed in 100 g of said solution, and was then subjected to vibration with an ultrasonic cleaner (available under the trade name of Ultrasonic Cleaner MU-III manufactured by GC Dental Industrial Corp.) for 20 minutes. Visual observation of the denture withdrawn from the solution revealed that tartar deposits were completely removed, and that the metallic and synthetic resin parts of the denture did not show any sign of abnormality. After the denture had been washed with water, followed by removal of the water by gauze wiping, it has been found to weigh 9.88 g, which meant that a weight loss corresponding to the tartar deposits was 0.16 g.

Example 3

Hydroxyethyylidenediphosphonic acid: 10 weight %
Ethylenediaminetetramethylphosphonic acid tetrasodium: 15.0 weight %
Aminotrimethylphosphroic acid hexasodium: 10 weight %
Purified wate: 63.5 weight %
Sodium lauryl sulfate: 1.0 weight %
Potassium chloride isocyanurate: 0.5 weight %

The aforesaid materials were mixed together under agitation to prepare a solution. Apart from this, a full denture comprising porcelain, methacrylic resin and a nickel-chromium alloy and found to have tartar deposits thereon over a wide range was removed from within the mouth of a patient, and was washed with water, followed by removal of the water by gauze-wiping. By measurement, it was found to have a weight of 27.46 g. The denture was immersed in 100 g of said solution, and was subjected to vibration with an ultrasonic cleaner (availalbe under the trade name of Ultrasonic Cleaner MU-III manufactured by GD Dental Industrial Corp.) for 30 minutes. Visual observation of the full denture withdrawn from the solution indicated that the tartar deposits were completely removed, and the porcelain, methacrylic resin and nickel-chromium alloy parts did not show any sign of abnormality. After the full denture had been washed with water, followed by removal of the water by gauze-wiping, it was found to have a weight of 26.86g, which meant that 0.60 g of the tartar deposits were removed.

Example 4

Aminomethylphosphonic acid: 8.0 weight %
Hydroxyethylidenediphosphonic acid: 10.0 weight %
Purified water: 79.0 weight %
Sodium alpha-olelfin sulfonate: 0.5 weight %
Deodorant (Trade Name - FS-500M - manufactured by Nippon Phirine Co., Ltd.): 2.0 weight %
Potassium chloride isocyanurate: 0.5 weight %

The aforesaid materials were mixed together under agitation to prepare a solution. Apart from this, a partial denture comprising a Ni-Cr alloy, porcelain and methacrylic resin and found to have tartar deposits thereon was removed from within the mouth of a patient, and was washed with water, following which the water was wiped out by gauze. By measurement, it was found to have a weight of 17.32 g. The denture was immersed in 100 g of said solution, and was subjected to vibration with an ultrasonic cleaner (available under the trade name of Ultrasonic Cleaner MU-III manufactured by GD Dental Industrial Corp.) for 20 minutes. Visual observation of the denture withdrawn from the solution revealed that the tartar deposits were completely removed.

The materials forming the denture did not show any sign of abnormality. After the denture had been washed with water, followed by removal of the water by gauze-wiping, it was found to weigh 17.03 g, which meant that a weight loss from removal of the tartar deposits was 0.29 g.

Comparative Example 1

Ethylenediaminetetramethylphosphonic acid: 8 weight %
Sodium tripolyphosphate: 15 weight %
Sodium alpha-olefin sulfonate: 0.2 weight %
Purified water: 76.8 weight %

The aforesaid materials were mixed together under agitation to prepare a solution. Apart from this, a full denture comprising porcelain and methacrylic resin, on which tartar was found to be deposited, was removed from within the mouth of a patient, and was washed with water, following which the water was wiped out by gauze. By measurement, it was found to have a weight of 18.30 g. The denture was immersed in 100 g of said solution, and was subjected to vibration with an ultrasonic cleaner (available under the trade name of Ultrasonic Cleaner MU-III manufactured by GC Dental Industrial Corp.) for 60 minutes. Visual observation of the full denture withdrawn from the solution indicated that the porcelain and methacrylic resin parts did not show any sign of abnormality, but some tartar deposits remained. After the denture had been washed with water, followed by removal of the water by gauze-wiping, it was found to have a weight of 18.28 g, which meant that the comparative solution was substantially ineffective, as seen from the fact that a weight loss from removal of the tartar deposits was only 0.02 g.

TABLE

| | Immersion time (min) | Weight loss due to removal of tartar (g) | Visual observation of prosthesis from which tartar was removed |
|---|---|---|---|
| Example 1 | 20 | 0.32 | Complete removal of tartar |
| Example 2 | 20 | 0.16 | " |
| Example 3 | 30 | 0.60 | " |
| Example 4 | 20 | 0.29 | " |
| Comparison Example 1 | 60 | 0.02 | Some tartar deposits remained |

As will be appreciated from the examples given hereinbefore, the agents for cleaning and dissolving tartar of removable oral prostheses make it possible to remove tartar deposits within an immersion time of 30 minutes or shorter without giving any damage to the prostheses.

Containing 8 weight % of ethylenediaminetetramethylphosphonic acid (the phosphorate base chelating agent), Comparative Example 1 was found to be less effective, since the amount of removal of tartar deposits on the full denture was only small.

What is claimed is:

1. An agent for cleansing and dissolving the tartar of removable oral prostheses consisting of a solution in water in amount of 35 to 90 wt.% of a mixture of aminotrimethylphophonic acid and hydroxyethylidenephosphonic acid or their alkali metal salts and an effective amount of at least one of a surfactant, a deodorant, a disinfectant, a deodorizer or a perfume, balance water, the solution having a pH of 7 or lower.

2. An agent for cleaning and dissolving tartar of removable oral prostheses consisting of a solution in water in an amount of 35 to 90 wt.% of a mixture of hydroxyethylidenephosphonic acid and ethylenediaminetetramethylphosphonic acid, or a mixture of hydroxyethylidene phosphonic acid, ethylenediaminetetramethylphosphonic acid and aminotrimethylphosphonic acid, or their alkali metal salts, and an effective amount of at least one of a surfactant, disinfectant, deodorant, deodorizer and perfume, the solution having a pH not greater than 7.

3. An agent for cleaning and dissolving tartar of removable oral prostheses consisting of the following composition:
Hydroxyethylidenediphosphonic acid: 10 weight %
Ethylenediaminetetramethylphosphonic acid tetrasodium: 15.0 weight %
Aminotrimethylphosphonic acid hexasodium: 10 weight %
Purified water: 63.5 weight %
Sodium lauryl sulfate: 1.0 weight %
Potassium chloride isocyanurate: 0.5 weight %.

* * * * *